United States Patent [19]

Monin et al.

[11] Patent Number: Plant 5,803

[45] Date of Patent: Nov. 18, 1986

[54] CHERRY ROOTSTOCK-GM G1/1 CULTIVAR

[75] Inventors: André Monin, Namur; Richard Trefois, Charleroi, both of Belgium

[73] Assignee: N.V. Jo Nicolai & Co., Duras, Belgium

[21] Appl. No.: 604,060

[22] Filed: Apr. 26, 1984

[51] Int. Cl.[4] ..... A01H 5/00

[52] U.S. Cl. ..... Plt./37

[58] Field of Search ..... Plt./37

[56] References Cited

U.S. PATENT DOCUMENTS

P.P. 4,059 6/1977 Tydeman ..... Plt./37

P.P. 5,159 12/1983 Tydeman ..... Plt./37

*Primary Examiner*—James R. Feyrer

*Attorney, Agent, or Firm*—Cushman, Darby & Cushman

[57] ABSTRACT

A new and distinct cultivar of cherry tree useful as a dwarfing, small-leaved cherry rootstock substantially as shown and described, discovered as a seedling among seedlings produced by open-pollination of offspring of a *Prunus dawyckensis* mother tree found growing in De Belder Nursery, Kalmthout, Belgium, which, when used as an understock, for sweet cherry trees, induces less growth of the sweet cherry tree, a semi-erect growth habit, a light canopy and early and abundant flowering and fruit setting.

9 Drawing Figures

BACKGROUND OF THE INVENTION

This new and distinctive cultivar of cherry rootstock was selected at Grand Manil, the Belgian experimental station from among seedlings produced by open pollination of the known species *Prunus dawckensis.* The mother tree came from a private arboretum, namely De Belder Nursery, Kalmthout, Belgium.

It has since been vegetatively propagated at the same place, both by herbaceous cutting under mist propagation, and by micropropagation in vitro. The plant has been found to be stable.

In comparison with standard characteristics of the known species *Prunus dawckensis,* the new cherry rootstock moderates the vigor of cherry trees grafted thereon, such that their height generally does not exceed 3.2 meters. Further, the new cultivar exhibits a capacity to propagate cuttings under mist propagation.

SUMMARY OF THE INVENTION

The new and distinct cultivar of cherry rootstock, which has been given the designation of GM G1/1 (in which the initial letters stand for Grand Manil, the Belgian experimental station), produces tree showing a semi-upright habit and of medium vigor, giving dwarf tree after grafting; said stock producing leaves which are small, in the range of 8–9 cm×4 cm, of which the form is oval with a very acuminate apex, the ratio length to width being higher than 2,1 and the greatest width of the leaf being situated under the middle of the leaf. The shape of the leaf is thus very elongated.

BRIEF DESCRIPTION OF THE DRAWINGS

The accompanying drawings show typical specimens of the new and distinct variety of cherry rootstock, wherein.

DETAILED DESCRIPTION

Figure 1:
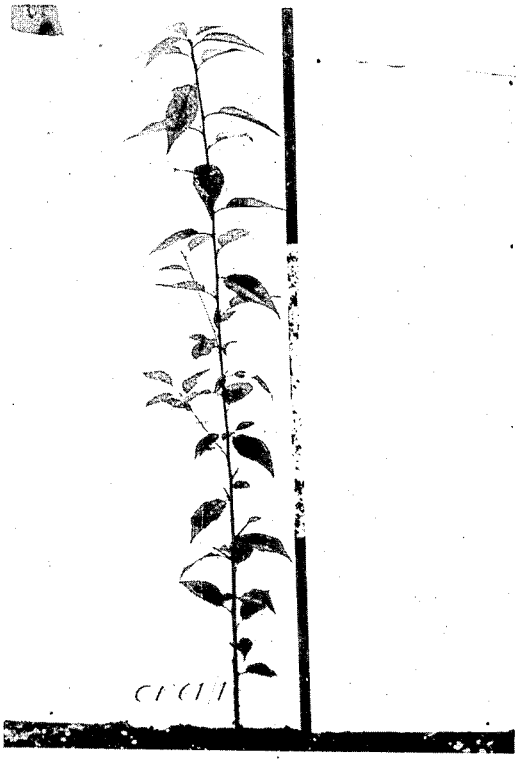
FIG. 1 shows a one year tree of the new cultivar of cherry rootstock.
Figure 3:
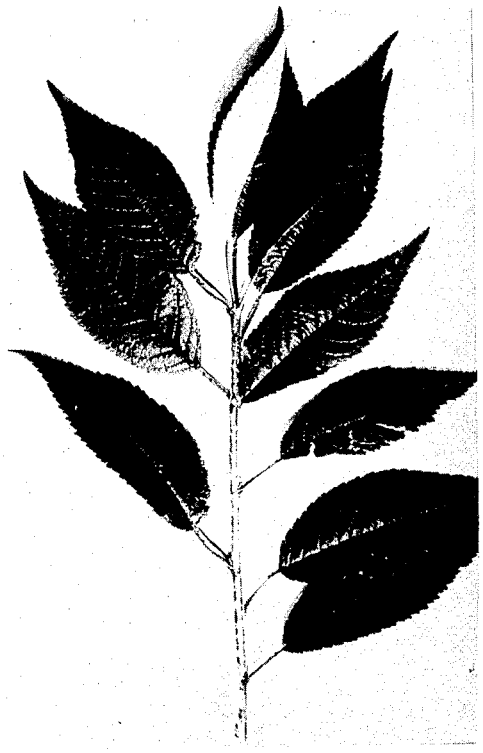
FIG. 3 shows the upper side of a foliate bough of the new cultivar of cherry rootstock.
Figure 2:
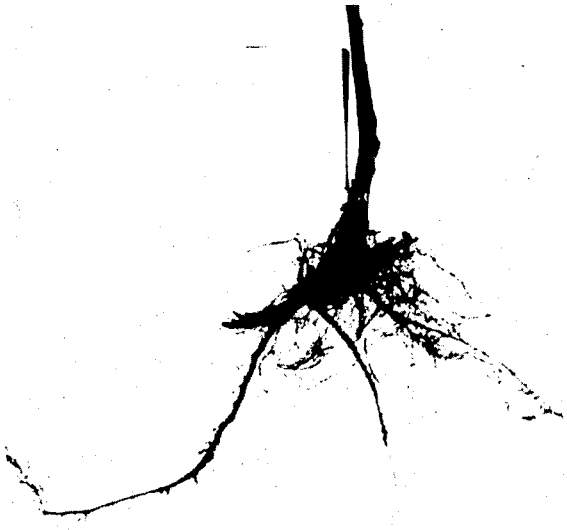
FIG. 2 shows the one year rooting system thereof.
Figure 4:
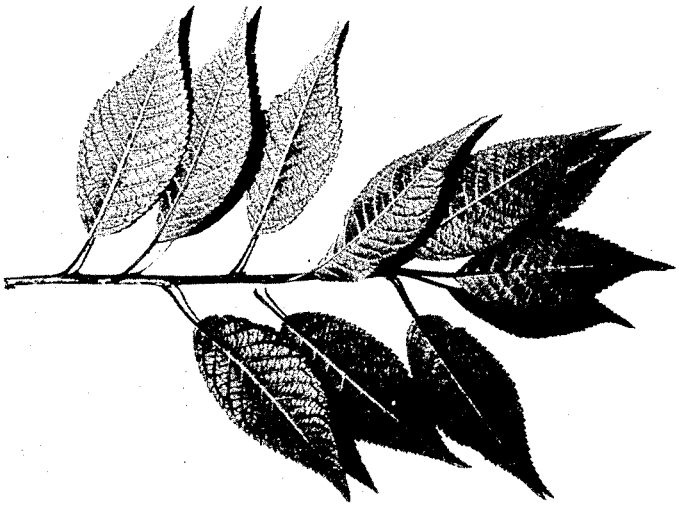
FIG. 4 shows the underside of a foliate bough thereof.
Figure 5:
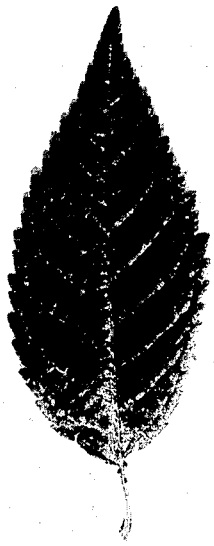
FIG. 5 shows the upper side of a leaf thereof.
Figure 6:
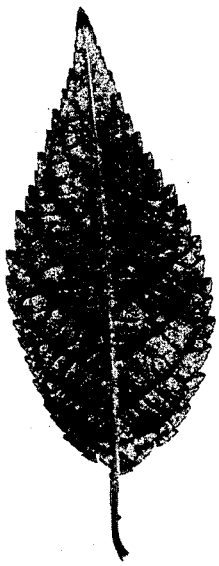
FIG. 6 shows the underside of a leaf thereof.
Figure 7:
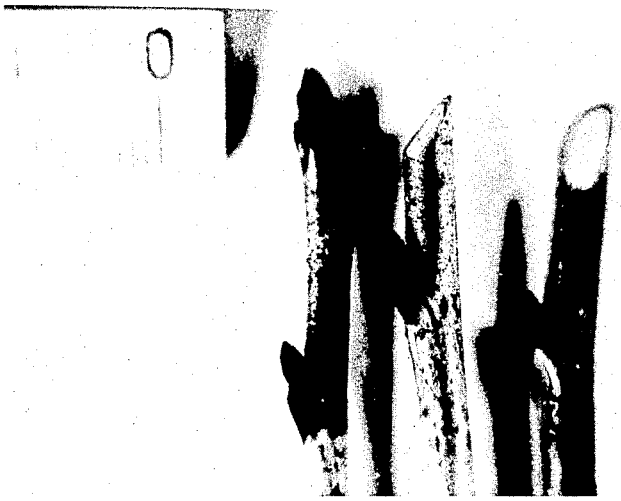
FIG. 7 shows details of buds thereof.
Figure 8:
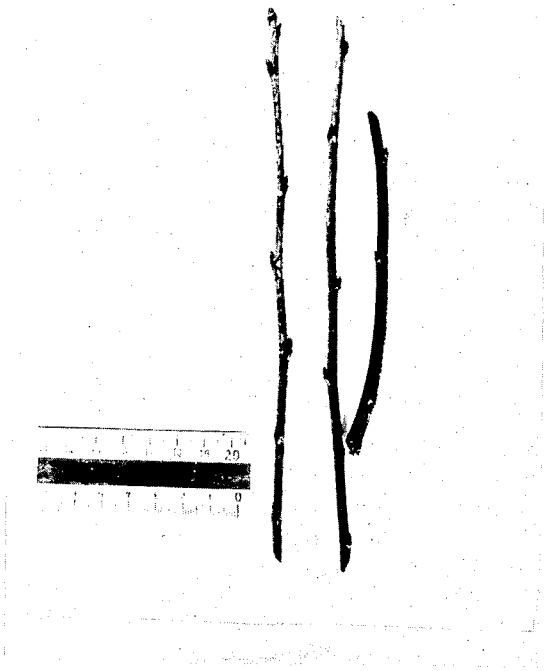
FIG. 8 shows segments of three non-foliated boughs thereof.
Figure 9:
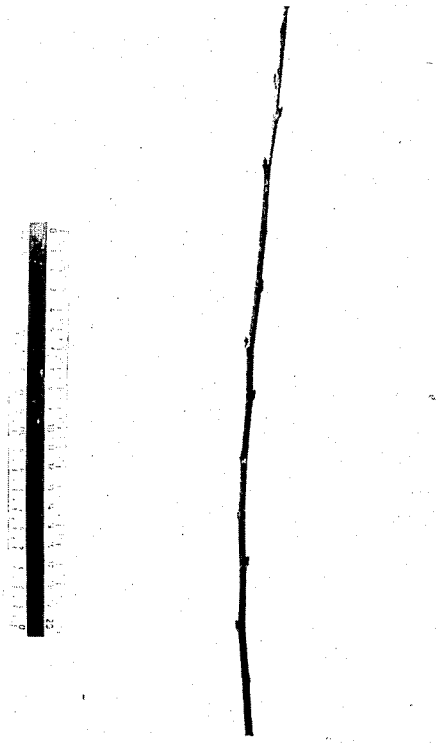
FIG. 9 shows an entire non-foliated bough thereof.

The new cultivar serves as a support for other cherry tree cultivars grafted thereon. Accordingly, the flowers, fruit and seed produced on the rootstock depend on the characteristics of the cherry tree cultivars which are grafted thereon.

The inflorescence, fruit and seed of the new cultivar itself have not been systematically observed.

The selected rootstock is semi-erected and shows moderate vigor.

The one year bough is brown at the base and gray-brown at the apex, with small lenticels.

The angle of the apex of the leaf is sharp (30°); it terminates regularly in a point with a gradual transition. The base of the leaf is sharp-pointed. The margin of the leaf is serrated, the indentation is double, the teeth are obtuse and show a crenulated configuration.

The upper face of the leaf is few pillose, the lower face is more villous especially the veins.

The color of the leaf is dark green and lustreless. The foliar venation is pennate with a tendency to become inflexed in the direction of the apex in the vicinity of the edges. Two to four irregularly disposed glands appear on the few pillose leaf petiole. Two glands are often observed at the base of the leaf.

The petiole is short, the ratio length of the leaf to length of the leaf petiole is higher than 4.3/1. No stipules were observed at the bases of the leaves.

Description of dormant plants

The buds are very thin (the length to width quotient is 2.2/1), and show an intermediate apex (between sharp pointed and rounded off).

Alternate buds lie flatly against the stern surface at swollen nodes. The prominence where the leaf is implanted is projecting. The leaf scale scar is large and triangular.

The apex of the twig contains several buds, among which the central one is much more highly developed than the others. The axillary buds are alone (2 small portions of these axillary buds are grouped by 2 or 3). In this last case, the central one is an eye bud; the other two ones are flower buds. The one year twigs are thick (about 6 mm diameter in the middle of the twig). The upper half of the one year twig is villous.

Physiology

Moderate vigor;

Opening of the buds takes place in the middle of the blooming season;

Fall of the leaves is normal;

Reddish foliage in autumn;

Good graft compatibility: tests to date indicate no problems with sweet cherries; the grafted tree shows a moderate vigor.

No or few throwing-out of suckers during cultivation;

Easy cultivation in nurseries.

The new cultivar has not been observed to be distinguished from the species per se by color.

Asexual propagation

Herbaceous cutting under mist propagation and micropropagation in vitro; the plant is thus stable.

Root well; creeping rooting.

The stock is cleaned against virus diseases by cultivation of merstems in vitro (mericlon No. F 3069) — (Reference of the Institute of Gemblox — Belgium).

The grafted trees are remarkable from the fact their height does not generally exceed 3.20 m. The canopy is light and the trees receive a maximum of sunning. The flowering and the fruit-setting are early and abundant.

We claim:

1. A new and distinct cultivar of cherry tree useful as a dwarfing, small-leaved cherry rootstock substantially as shown and described, discovered as a seedling among seedlings produced by open-pollination of offspring of a *Prunus dawyckensis* mother tree found growing in De Belder Nursery, Kalmthout, Belgium, which, when used as an understock, for sweet cherry trees, induces less growth of the sweet cherry tree, a semi-erect growth habit, a light canopy and early and abundant flowering and fruit setting.

* * * * *